(12) United States Patent
Nightengale

(10) Patent No.: US 12,263,290 B2
(45) Date of Patent: Apr. 1, 2025

(54) SYSTEM AND METHOD FOR CARDIORESPIRATORY SUPPORT

(71) Applicant: Christopher J. Nightengale, Littleton, CO (US)

(72) Inventor: Christopher J. Nightengale, Littleton, CO (US)

( * ) Notice: Subject to any disclaimer, the term of this patent is extended or adjusted under 35 U.S.C. 154(b) by 1204 days.

(21) Appl. No.: 17/071,828

(22) Filed: Oct. 15, 2020

(65) Prior Publication Data
US 2021/0106746 A1    Apr. 15, 2021

Related U.S. Application Data

(60) Provisional application No. 62/915,307, filed on Oct. 15, 2019.

(51) Int. Cl.
*A61M 1/36* (2006.01)

(52) U.S. Cl.
CPC ........ *A61M 1/3666* (2013.01); *A61M 1/3633* (2013.01); *A61M 1/3639* (2013.01); *A61M 1/3653* (2013.01); *A61M 2205/3327* (2013.01)

(58) Field of Classification Search
CPC .............. A61M 1/3666; A61M 1/3633; A61M 1/3639; A61M 1/3653; A61M 2205/3327

USPC ........................................................ 604/6.11
See application file for complete search history.

(56) References Cited

U.S. PATENT DOCUMENTS

| | | | | |
|---|---|---|---|---|
| 4,424,806 A | * | 1/1984 | Newman | A61H 9/0078 128/205.25 |
| 4,840,167 A | * | 6/1989 | Olsson | A61H 9/0078 601/106 |
| 2003/0131844 A1 | * | 7/2003 | Kumar | A61M 16/0081 128/200.24 |
| 2010/0319691 A1 | * | 12/2010 | Lurie | A61M 16/06 128/205.24 |
| 2011/0313332 A1 | * | 12/2011 | Rahman | A61H 31/00 601/41 |
| 2018/0104426 A1 | * | 4/2018 | Oldfield | A61M 16/024 |

* cited by examiner

*Primary Examiner* — Andrew J Mensh

(57) ABSTRACT

A method of circulating a flow of blood within a circulatory system of a body includes applying an extrathoracic pressure to the body with a fluid. An intrathoracic pressure is applied to the body with the fluid. The application of the extrathoracic pressure relative to the application of the intrathoracic pressure is varied, so as to circulate a flow of blood within the circulatory system of the body.

20 Claims, 9 Drawing Sheets

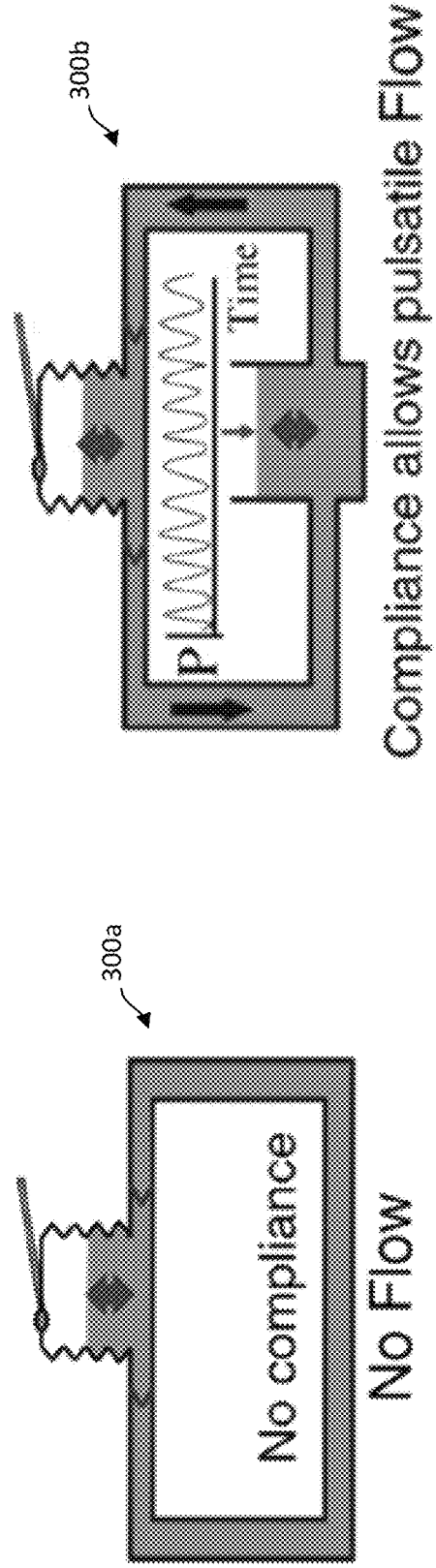
FIG. 3A
FIG. 3B
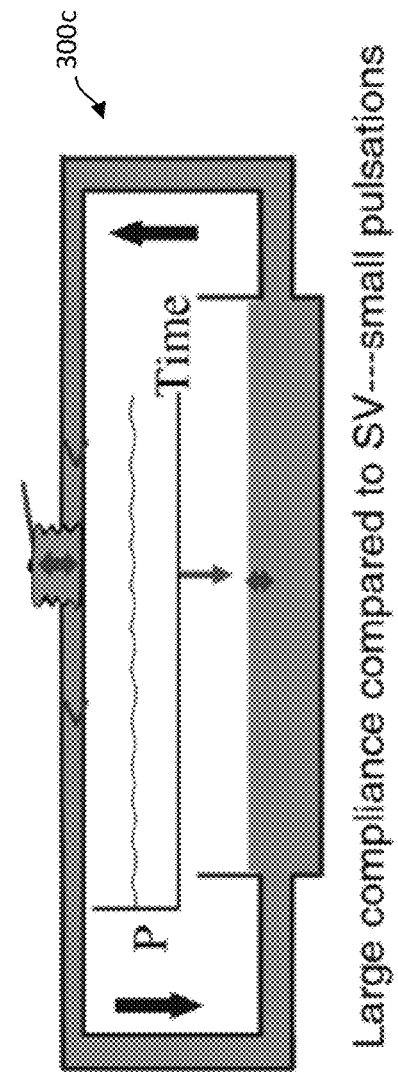
FIG. 3C

SYSTEM AND METHOD FOR CARDIORESPIRATORY SUPPORT

CROSS-REFERENCE TO RELATED APPLICATION

This application claims priority to and the benefit of U.S. Provisional Application Ser. No. 62/915,307, filed Oct. 15, 2019, entitled "SYSTEMS, DEVICES, AND METHODS FOR IMMERSIVE LIQUID VENTILATION, TORPOR, ANESTHETIZED STATE, AND POIKILOTHERMIC RESUSCITATION," the disclosure of which is hereby incorporated by reference herein in its entirety.

BACKGROUND

Liquid ventilation has been investigated and used since the 1960s, progressing from oxygenated saline solutions to perfluorocarbons. Liquid ventilation techniques have tested total liquid ventilation (TLV) using tidal volumes of oxygenated perfluorocarbons (PFC), partial liquid ventilation (PLV) which fills lungs to functional residual volume (FRV) with ventilation against an air/liquid interface, as well as PFC nebulization. Liquid ventilation has been used in neonates, pediatric patients, and adults. The technique has been used for patients with immature lungs and lung injury. Liquid ventilation has been shown to be beneficial for patients with severe lung abnormalities requiring ventilatory support for hypoxemia and respiratory failure.

Chilled ventilated PFC has also been shown to be an efficient method to provide rapid core hypothermia with an efficiency similar to cardiopulmonary bypass. PFC induced post cardiac arrest hypothermia has been widely tested in animal models and shows rapid changes in core temperature with improvements in neurologic function and return of spontaneous circulation (ROSC). PFCs are biologically inert, can carry high volumes of dissolved gases, decrease alveolar surface inflammatory molecules, irrigate secretions from the bronchial tree, and are safe to use with severe lung injury. Introducing PFCs into the lungs to FRV can cause cardiovascular instability as the PFC mass alters West lung zones, intrapulmonary pressure, and right atrial pressure. Adequate circulatory volume and slow filling to FRV reduces instability. In some cases, because of the increased viscosity, PFC mass, and resistance to flow of a liquid compared to a gas, breathing PFC spontaneously rapidly fatigues the respiratory muscles. Supportive mechanical ventilation may be necessary with TLV. Current generation liquid ventilators combine a positive pressure inspiratory cycle with a negative pressure expiratory cycle to assist with removal of inhaled PFC volumes.

SUMMARY

In one aspect, the technology relates to a method of circulating a flow of blood within a circulatory system of a body, the method including: applying an extrathoracic pressure to the body with a fluid; applying an intrathoracic pressure to the body with the fluid; and varying the application of the extrathoracic pressure relative to the application of the intrathoracic pressure, so as to circulate the blood flow within the circulatory system of the body. In an example, the method further includes receiving the body within a pressurization environment. In another example, applying the extrathoracic pressure includes pressurizing the pressurization environment with the fluid, wherein the fluid is pressurized by an extrathoracic pump. In yet another example, applying the intrathoracic pressure includes pressurizing the pressurization environment with the fluid, wherein the fluid is pressurized by an intrathoracic pump. In still another example, the method further includes circulating the fluid in a fluid circuit disposed outside of the body.

In another example of the above aspect, circulating the fluid further includes filtering the fluid. In an example, circulating the fluid further includes oxygenating the fluid. In another example, the method further includes introducing at least one medicament to the fluid. In yet another example, circulation of the blood flow within the circulatory system of the body is sufficient to preserve a function of at least one organ of the body. In still another example, the method further includes detecting the circulation of the blood flow within the circulatory system of the body and varying the application of the extrathoracic pressure relative to the application of the intrathoracic pressure based at least in part on detecting the circulation of the blood flow within the circulatory system of the body.

In another aspect, the technology relates to a system for circulating a blood flow within a circulatory system of a body, the system including: a pressurization vessel, wherein the pressurization vessel comprises a pressurization volume and a receiver configured to at least partially receive the body; an extrathoracic pump fluidically coupled to the pressurization volume; an intrathoracic pump configured to be fluidically coupled to a controlled airway device inserted into the body; and a fluid treatment circuit fluidically coupled to the extrathoracic pump and the intrathoracic pump. In an example, the fluid treatment circuit includes at least one of a fluid heater, a fluid filter, a fluid oxygenator, a fluid carbon dioxide scavenger, a fluid reservoir, and a fluid medicament introduction structure. In another example, at least one of the extrathoracic pump and the intrathoracic pump includes a dynamic pump. In yet another example, the pressurization vessel includes: an exterior shell; and an interior bladder disposed within the exterior shell, wherein the interior bladder defines the pressurization volume and at least partially defines the receiver. In still another example, the exterior shell is integral with the interior bladder.

In another example of the above aspect, the exterior shell is rigid and the interior bladder is flexible. In another example, the system further includes: a controller communicatively coupled to the extrathoracic pump and the intrathoracic pump; and a sensor for sensing the blood flow within the circulatory system of the body. In yet another example, the sensor includes an ultrasound sensor. In still another example, the pressurization vessel includes a pressurizable sleeve.

In another aspect, the technology relates to a system including: a pressurization vessel comprising a pressurizable bladder and a port configured to connect the pressurizable bladder to a fluid pump, wherein the pressurizable bladder at least partially defines a receiver for receiving a body; a sensor for detecting a condition within the body when the body is received within the receiver; and a controller configured to be communicatively coupled to the sensor, wherein the controller comprises at least one auxiliary input for connecting the controller to the fluid pump.

BRIEF DESCRIPTION OF THE DRAWINGS

FIGS. 3A-3C depict models of systems having varying levels of compliance.

DETAILED DESCRIPTION

In addition to the background detailed above, the present disclosure is made in light of the following principles: (i) mammalian metabolic rate decreases by about 8% for each 1 degree Celsius decrease in core temperature; (ii) human evolution does not include torpor or hibernation; (iii) long term stasis must include a low friction, low surface pressure, inert, environment; (iv) at times during stasis, controlled cardiorespiratory status will be necessary; (v) torpor and hypothermia require decreased consciousness and protection from the surrounding environment; (vi) increased dependence on the thoracic pump for circulation as core temperature decreases with associated bradycardia and decrease in cardiac output; (vii) controlled temperature can affect multiple enzymatic, metabolic, genomic, inflammasomic, proteonomic, and endocrine pathways, and (viii) prolonged immersed supported state requires fluids, nutrients, and multiple categories of medications.

Figure 1:
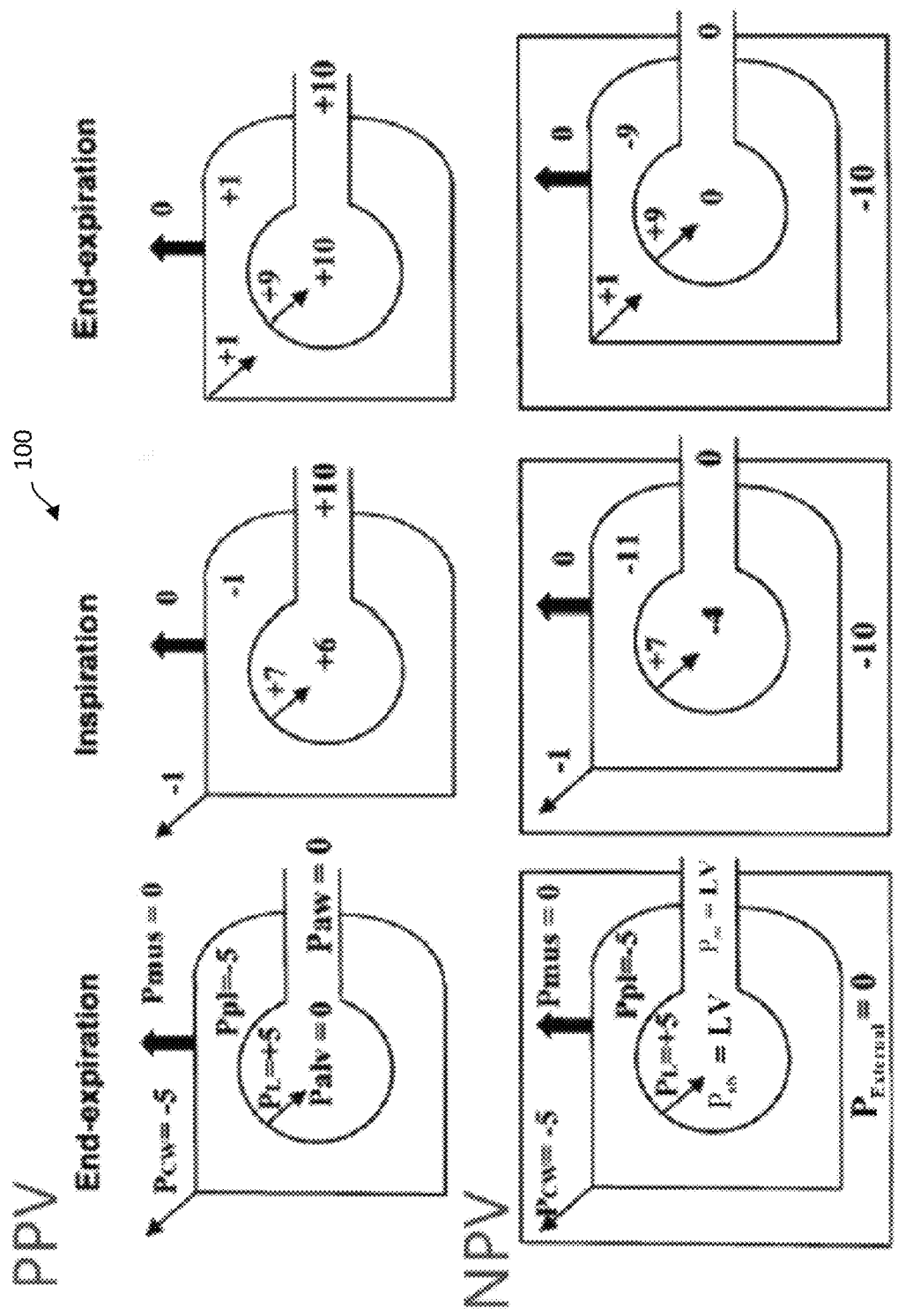
FIG. 1 depicts models of airway pressure, intrathoracic pressure, and extrathoracic pressure during positive pressure (PPV) and negative pressure (NPV) ventilation.

FIG. 1 depicts models 100 of airway pressure, intrathoracic pressure, and extrathoracic pressure during positive pressure (PPV) and negative pressure (NPV) ventilation. Compliance is the change in volume in response to a change in pressure. Vascular compliance is the ratio of change in vascular volume in response to a change in pressure. For the purpose of analysis, the vascular system can be modeled as a group of volume compartments connected in parallel and series. The heart, kidneys, sympathetic-parasympathetic innervation, and endocrine system regulate blood volume, blood flow, arterial/venous resistance, and cardiac output. Among others, a previous attempt to model the vascular system involved using an open-chest canine technique. This model detailed the relationships between cardiac output, systemic resistance, blood pressure, venous return, and right atrial pressure. This model combined open-loop cardiac output and venous return functions into a closed function by superimposing the experimentally derived venous return curve on the cardiac output curve. Unstressed blood volume is the content of the vascular tree that fills but does not pressurize the circulation. The pulsatile cardiac output then adds stressed volume to the vascular system that pressurizes the vasculature. Combining cardiac output with an estimate of vascular system resistance it is possible to calculate pressures in various parts of the circulation. Examples of mathematical and computational modeling of the cardiovascular system include the following disclosures: Heldt, Thomas et al. "CVSim: An Open-Source Cardiovascular Simulator for Teaching and Research." *The open pacing, electrophysiology & therapy journal* vol. 3 (2010): 45-54; Noordergraaf, G., Ottesen, J., Kortsmit, W. et al. The Donders Model of the Circulation in Normo- and Pathophysiology. *Cardiovasc Eng* 6, 51-70 (2006); Noordergraaf, G. "Cardiopulmonary Resuscitation: are two hands (really) enough? A modeling approach to CPR." (2009). The disclosures of the above-identified references are hereby incorporated by reference herein in their entireties.

In the intact human circulation, a mean systemic filling pressure of approximately 6-7 cm $H_2O$ is the driving pressure for central venous return. The equation describing venous return is:

$$VR = \frac{P_{MS} - P_{RA}}{R_{VR}} \quad \text{(Eqn. 1)}$$

In Equation 1, VR is venous return, $P_{MS}$ is mean systemic pressure (or mean surface filling pressure), $P_{RA}$ is right atrial pressure, and $R_{VR}$ is resistance to venous return.

Because $P_{MS}$ is stressed volume divided by venous compliance, the relationship between external pressures and venous return can further be described as $$VR = \frac{\frac{\gamma}{C_v} - P_{RA}}{R_{VR}} \quad \text{(Eqn. 2)}$$

In Equation 2, γ is stressed volume and $C_v$ venous compliance.

Figure 2:
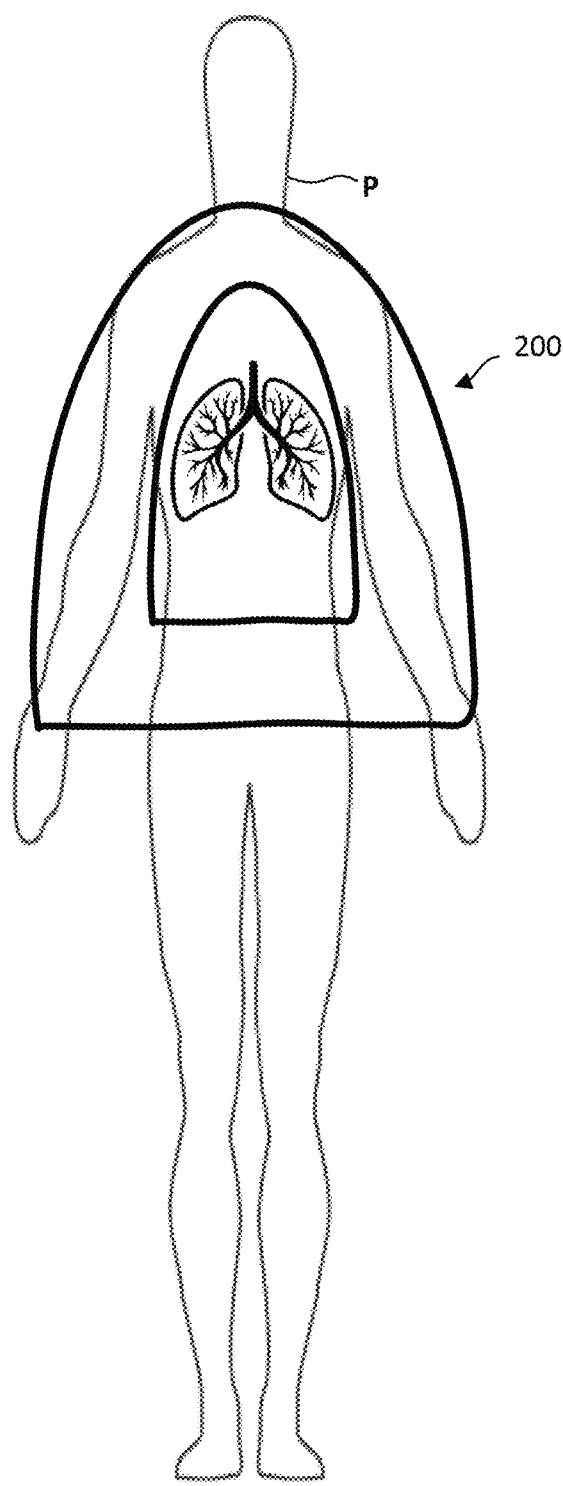
FIG. 2 depicts a model of a patient placed in an immersive ventilator.

FIG. 2 depicts a model of a patient P placed in an immersive ventilator 200. Ventilation techniques, described in greater detail elsewhere herein, include filling the pulmonary volume with PFC or similar fluid, surrounding the patient with the fluid, and applying pressure changes. As used herein, a fluid can include a liquid, a gas, a plasma, or any combination of the above. Through these operations, the pulmonary TLV and external PFC volumes may be effectively linked PPV/NPV systems separated by the chest wall and diaphragm yet connected through the intrathoracic and body surface pressures. The system fluid can then, in various embodiments, be cycled, filtered as needed, oxygenated, and temperature controlled. Consistent with the techniques and systems described herein, controlling the intrathoracic and external surface pressure to the patient may have desirable effects on cardiac output, right atrial pressure, preload, and afterload.

The respiratory effects of such a system may be modeled. In an immersive ventilator system, such as depicted in FIG. 2, the numerator and denominator in Equation 1 (above), as well as respiratory pressures and volumes may be manipulated. $P_{MS}$ is generally not directly affected by the heart or circulatory resistances, but rather depends on stressed volumes and compliances in the systemic circulation. As an example, during cardiac arrest, as pulsatile pressure ceases and blood volume redistributes, the immediate residual circulatory pressure is $P_{MS}$. $P_{MS}$ and $P_{RA}$ then equalize, and VR is zero. In a submerged state (e.g., when a patient is disposed in an immersive ventilator, such as depicted in FIG. 2), venous compliance is dependent on the surface pressure and $P_{MS}$ can be manipulated by changing surface pressure during the cardiac cycle. Blood volume can be moved into the pulmonary and arterial circulation by altering intrathoracic pressures in either a positive or negative direction. The physiologic valves contained within the peripheral microcirculation encourage unidirectional blood flow. In this way, cardiac output can be assisted or limited by changing cardiac preload and afterload through intrathoracic and peripheral surface changes.

FIGS. 3A-3C depict models of systems 300a, 300b, and 300c having varying levels of compliance. Specifically, in FIG. 3A, a system 300a having no compliance does not allow flow in response to a pulsatile energy source. In FIG. 3B, compliance allows flow in response to a pulsatile energy source in depicted system 300b. In FIG. 3C, compliance is large compared to surface volume, which may approximate the venous vasculature of humans under normal conditions, as depicted in system 300c. The following equations provide a mathematical model of flow in a circulatory system. Beginning with an equation modeling venous return:

$$VR = \frac{P_{MS} - P_{RA}}{R_{VR}} \qquad (\text{Eqn. 3})$$

If $P_{MS}-P_{RA}$ is a driving pressure in normal circulation, then Thoracic Pump Pressure (TPP) would be approximately $P_{MS}-P_{RA}$ during asystole. In cardiac arrest, $P_{MS}=P_{RA}$, VR=0; $P_{RA}$=intrathoracic pressure; $P_A$=alveolar pressure=liquid, or gas ventilation pressure=$P_{LA}$; $P_{LEXT}$=external supporting gas or liquid fluid pressure; $P_{MS}=P_{CV}$ (central venous pressure). At asystole, central venous pressure is approximately atmospheric pressure, which is zero by definition of atmospheric pressure as a reference pressure. However, under application of nonzero extrathoracic pressure, reference pressure is no longer atmospheric pressure. Rather, $P_{MS}=P_{CV}=P_{EXT}=P_{LEXT}$. Through substitution, the equation for venous return becomes:

$$VR = \frac{P_{LEXT} - (P_{LEXT} - P_{LA})}{R_{VR}} = \frac{P_{LA}}{R_{VR}} \qquad (\text{Eqn. 4})$$

These derived equations are consistent with expectations for an asystolic patient. During cardiac arrest with chest compression it has been assumed that the thoracic pump is the mechanism for blood flow during resuscitation. The above analysis suggests that compression of the thorax alone is enough to act as a driving pressure to induce circulation, even though the intrathoracic pressures provided by chest compressions do not sum to zero with rebound of the chest wall. This is where the one-way flow and compliance differences in the thorax and peripheral circulation become relevant, allowing for generation of a more general set of equations and extending the analysis of cardiac output or VR to include systole. However, cardiac resuscitation with chest compression results in poor cardiac output and uniformly poor survival for patients in cardiac arrest.

During systole and ventilation in an immersive ventilator, venous return is approximated by the general equation for cardiac output from a venous return perspective:

$$VR = \frac{P_{LA}}{R_{VR}} + \frac{P_{MS} - P_{RA}}{R_{VR}} \qquad (\text{Eqn. 5})$$

where $P_{LA}$ is defined relative to a reference pressure, which in an immersive ventilator, can be the extrathoracic pressure, or $P_{LEXT}$. Rearranging and substituting:

$$VR = \frac{P_{LEXT} - P_{LV} + P_{MS} - P_{RA}}{R_{VR}} \qquad (\text{Eqn. 6})$$

In the time domain, this provides a general equation of cardiac output:

$$\text{Cardiac Output } (t) = \int_0^t \frac{P_{LEXT}(t) - P_{LV}(t) + P_{MS}(t) - P_{RA}(t)}{R_{VR}(t)} dt \qquad (\text{Eqn. 7})$$

Using the systems and techniques described herein, $P_{LEXT}(t)$ and $P_{LV}(t)$ with fluid ventilation can be either positive or negative within physiologic ranges, enabling control over the total Cardiac Output (t) by manipulation of the pressures at various points in a system. An example of predicted Cardiac Output (t) in light of the background models discussed previously is depicted below.

Figure 4:
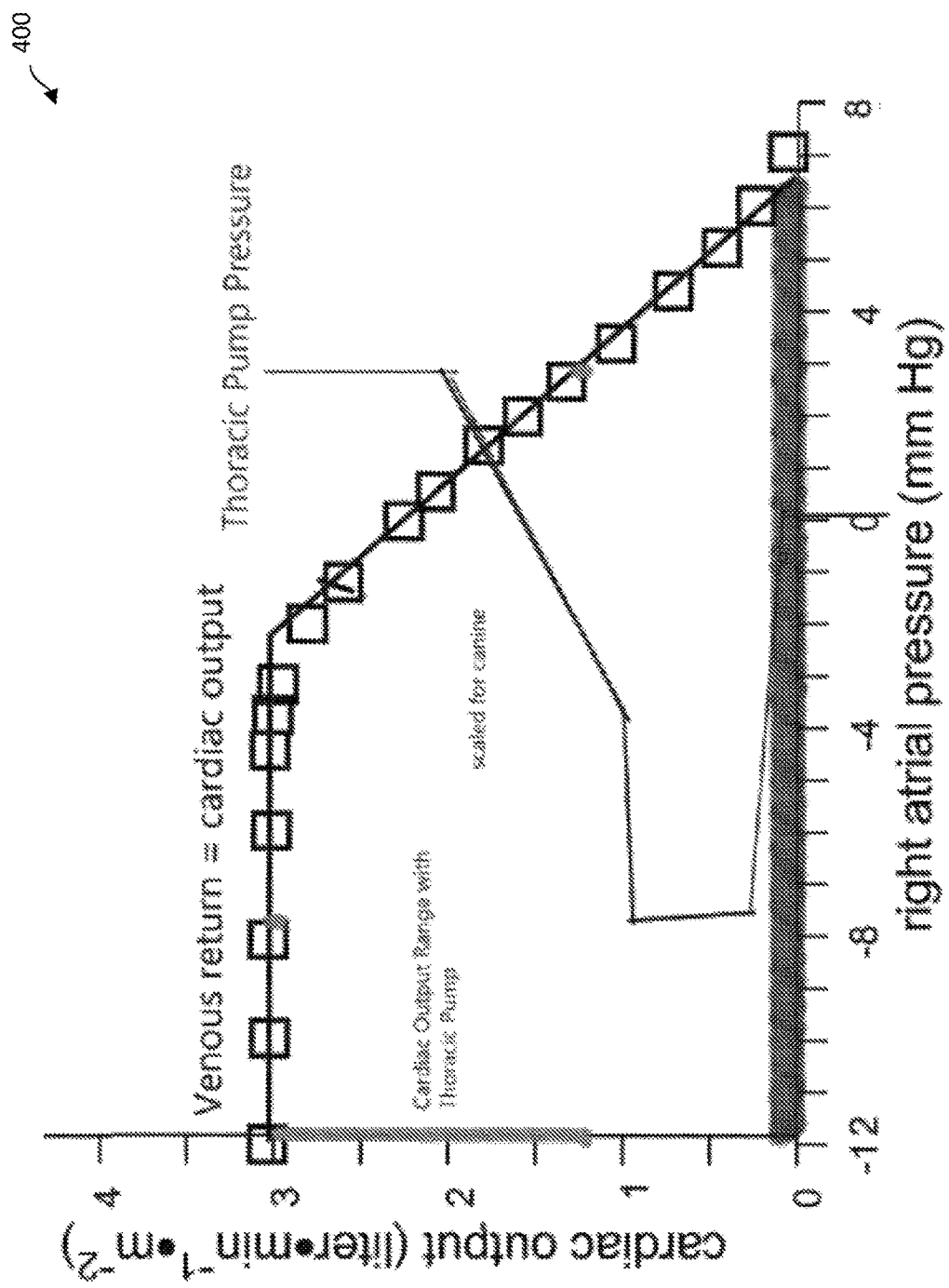
FIG. 4 depicts a graphical representation of modeled cardiac output mapped on a venous return curve.

FIG. 4 depicts a graphical representation of modeled cardiac output mapped on a venous return/cardiac output curve. The graph 400 shows an example of the modeled effects of capacitance changes on normal cardiac output and a superimposed thoracic pump pressure graph. As depicted, venous return can be plotted against right atrial pressure. The model shows that Thoracic Pressure Pump is approximately $P_{MS}$–RAP during asystole. Overlaying an example thoracic pump pressure range shows a potential cardiac output range for an example canine model using the immersive ventilation techniques and systems described herein. The graphical representation demonstrates how varying $P_{MS}$ and RAP may affect venous return and cardiac output, thereby creating a cardiac output assist device that can induce a flow of blood in the body, or support cardiac output with a failing heart, by applying an intrathoracic pressure and an extrathoracic pressure (e.g., through the method depicted in FIG. 8 below).

Figure 5:
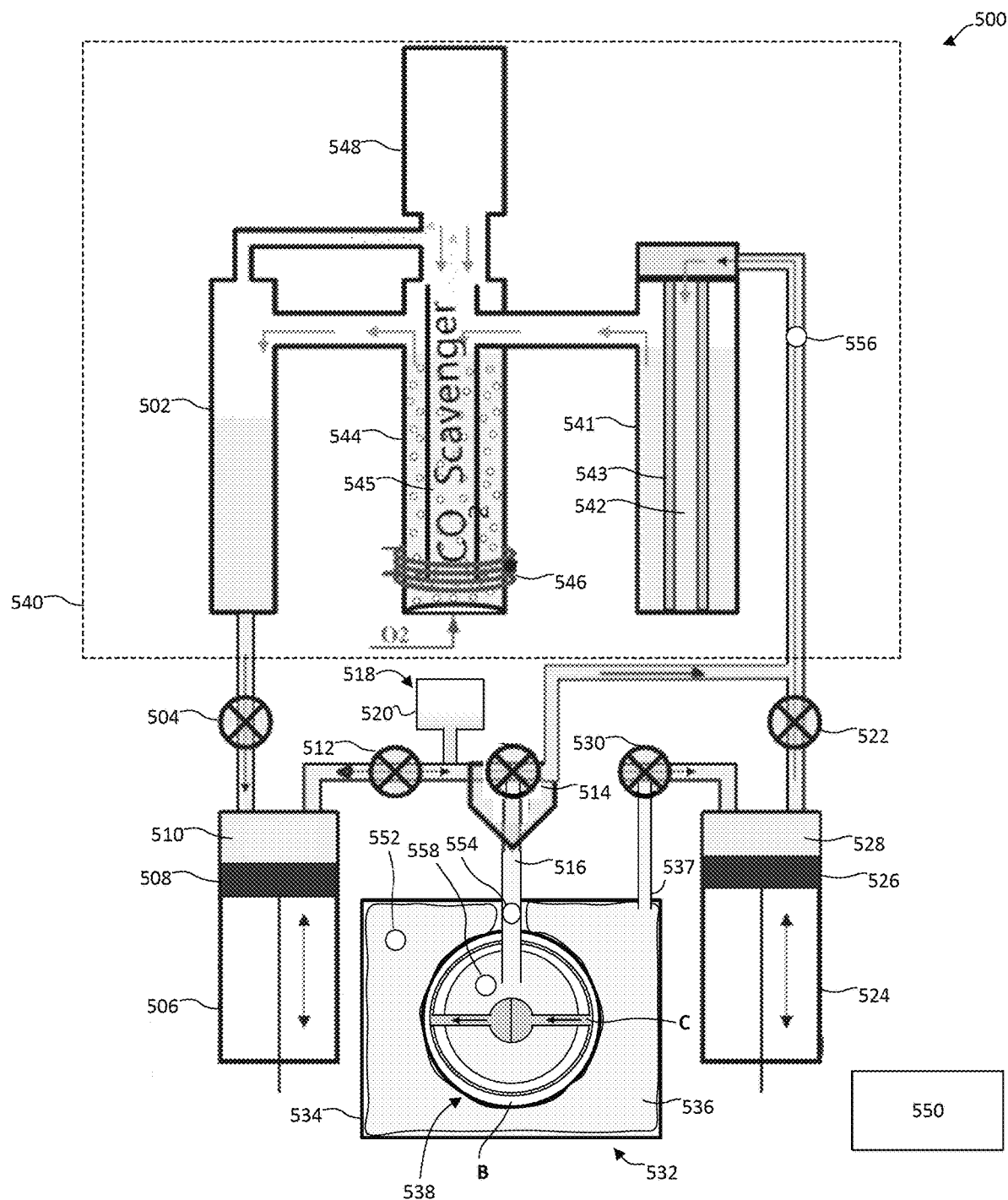
FIG. 5 is a schematic view of an example of a cardiovascular pumping system.

FIG. 5 depicts a schematic view of an example of a cardiovascular pumping system 500 for a body B. The cardiovascular pumping system 500 includes a fluid reservoir 502. The fluid reservoir 502 may be a volume of any shape or size sufficient to contain a fluid used in the system 500. Suitable fluids may be a liquid or a gas and may include, for example, a perfluorocarbon ("PFC") or any physiologically inert and nontoxic fluid.

Fluid reservoir 502 may be fluidly connected to intrathoracic pump 506. In examples, fluid reservoir 502 and intrathoracic pump 506 are separated by a valve 504. Valve 504 may be any type of valve, such as, e.g., a ball valve, pinch valve, check valve, or needle valve and may be two position (e.g., ON/OFF) or may provide a variable flow therethrough. The valve 504 may utilize an automatic actuator or may be manually operable. Intrathoracic pump 506 may be any type of pump suitable for pressurizing a fluid. In an example, intrathoracic pump 506 is a pump that guarantees delivery of a volume of fluid at a regulated pressure, such as a dynamic pump. In the system 500, intrathoracic pump 506 includes a piston 508, configured to apply a positive pressure or a negative pressure to the fluid disposed in the pump chamber 510.

The intrathoracic pump 506 may be configured to apply an intrathoracic pressure to an intrathoracic volume of a body B, by delivering pressurized liquid via a controlled airway device 516 into the body B. As used herein, a controlled airway device may be an endotracheal tube, tracheostomy, or any other suitable device for controlling a flow of fluid into a body B. More specifically, intrathoracic pump 506 introduces a volume of the fluid into the lungs of the body B. In examples, intrathoracic pump 506 and controlled airway device 516 are separated by valves 512 and 514, which may be similar to valve 504 (e.g., with regard to type, flow rate, etc.) and may further control the flow of fluid between intrathoracic pump 506 and controlled airway device 516.

A medicament introduction device 518 may include a medicament reservoir 520. Medicament introduction device 518 may introduce a medicament from medicament reservoir 520 into the fluid flowing from intrathoracic pump 506 so as to control the administration of a medicament to the body B. The medicament introduction device 518 may, for example, introduce any one or more of, independently or in combination, a pharmaceutical drug, a liquid mixture, a liquid compound, a solution, a gaseous compound, a solid compound, a vapor, etc.

Controlled airway device 516 may further be fluidly connected with fluid circuit 540 and, via valve 522, to extrathoracic pump 524. Valve 514 separating intrathoracic pump 506 and controlled airway device 516 may, in certain examples, be a diversion valve that diverts a portion of the flow of fluid simultaneously towards the controlled airway device 516 and away from the controlled airway device 516 (e.g., towards circuit 540). As such, valve 514 may further control fluid flow into the lungs, e.g., to avoid overpressurization thereof which may lead to rupture or other damage. Similar to intrathoracic pump 106, extrathoracic pump 524 may be any type of pump suitable for pressurizing a fluid, such as a pressure-regulated, volume-guaranteed delivery system, such as a dynamic pump. Extrathoracic pump includes piston 526, configured to apply positive or negative pressure to pump chamber 528. Accordingly, when diversion valve 514 is positioned to allow flow between the controlled airway device 516 and extrathoracic pump 524 and when valve 522 is likewise positioned to allow fluid flow, extrathoracic pump 524 may draw a fluid from the body B into the pump chamber 528. In this manner, extrathoracic pump 524 may decrease the pressure applied to the intrathoracic volume of the body B. In certain examples, extrathoracic pump 524 may apply a negative pressure (e.g., relative to a reference pressure) to the intrathoracic volume of the body B. As is discussed in greater detail elsewhere herein, such a pressure decrease (e.g., relative to a mean systemic pressure of the body B) may create a pressure gradient between an intrathoracic pressure and a pressure elsewhere in the body B and may, as a result, induce a flow of blood from the body B into the heart and ventilate the lungs of the body B.

Extrathoracic pump may further be fluidly connected with pressurization vessel 536 that may include pressurization shell 534 and pressurization volume 536. In examples, pressurization volume 536 is a pressurizable bladder. Pressurization volume 536 may further define a receiver 538 into which a body B (e.g., human or other animal) may be received. Pressurization volume 536 may further include a port 537 for fluidly connecting the pressurization volume 536 with extrathoracic pump 524. Extrathoracic pump 524 and port 537 may be separated by valve 530, which may be actuated to allow or otherwise control flow between extrathoracic pump 524 and pressurization volume 536. Extrathoracic pump 524 transfers fluid from pump chamber 528 to pressurization volume 536. In this manner, extrathoracic pump 524 may increase the pressure applied to a surface of the body B, which has been received by the receiver 538 of the pressurization volume 536.

Upon introduction of a fluid into pressurization volume 536, pressurization volume 536 may expand within pressurization vessel 532 (e.g., within the pressurization shell 534). During such expansion, pressurization volume 536 may exert pressure at the surface of the body B in the receiver 538. Pressurization volume 536 may exert pressure at select locations or on select parts of the body B (e.g., at one or more extremities or limbs) of the body B or may exert pressure over substantially the entire surface of a body B. For instance, pressurization volume 536 may, as depicted, receive an entire body B. In other examples, pressurization volume 536 may receive only a torso of the body B. In such examples, expansion of pressurization volume 536 may exert pressure to the surface of the torso of the. In any of these configurations or in any other configuration that would be appreciated by a person of skill in the art, application of a pressure to one or more surfaces of the body B received in the pressurization volume 536 may be used to create a positive or negative pressure differential (e.g., "gradient") within the body B. For instance, the application of a pressure to a surface of the body B (e.g., by introduction of a fluid to the pressurization volume by the extrathoracic pump) may increase a pressure in the vascular system of the body B (e.g., a mean systemic pressure). Such an increase may create a pressure differential between the systemic pressure and an intrathoracic pressure (e.g., a pressure of the right atrium). As is discussed in greater detail elsewhere herein, such a pressure gradient between an intrathoracic pressure and a pressure elsewhere in the body B and may induce a flow of blood from the body B into the heart (e.g., a venous return).

Extrathoracic pump 524 is further fluidly connected to a fluid treatment circuit 540 that fluidly connects extrathoracic pump 524 with fluid reservoir 502. In such a configuration, system 500 becomes a "closed circuit" in which fluid originating in fluid reservoir 502 circulates from intrathoracic pump 506 to extrathoracic pump 524 before returning to fluid reservoir 502. In an example, fluid treatment circuit 540 includes one or more components for treating the fluid before it returns to fluid reservoir 502. For example fluid treatment circuit 540 may include filter 541 fluidly connected with extrathoracic pump 524. Filter 541 may include a filter volume 542 and a filter element 543. Fluid flowing through filter 541 may enter filter volume 542 and may flow through filter element 543. Filter element 543 may remove, among other things, particulates, chemical compounds, or any other solid, fluid, or gaseous matter present in the fluid flowing from extrathoracic pump 524 into fluid treatment circuit 540. Filter 541 is fluidly connected with oxygenator 544, which may include any one or more of $CO_2$ scavenger 545, heater/cooler 546, and condenser 548. As a person of skill in the art will appreciate, fluid flowing from filter 541 to oxygenator 544 (e.g., by expansion of intrathoracic pump 506 and/or compression of extrathoracic pump 524) may contain a concentration of dissolved carbon dioxide. Accordingly, oxygenator 544 may, using $CO_2$ scavenger 545, condenser 548, and heater/cooler 546, remove an amount of dissolved carbon dioxide from the fluid and introduce an amount of oxygen. Thus, the fluid in fluid reservoir 502 may, when introduced into the lungs of a body B received in the pressurization vessel 532, provide an amount of oxygen to the circulatory system of the body B (e.g., through the pulmonary circulation system of the body B). In an alternate embodiment, a fluid treatment circuit directly connects an extrathoracic pump and a fluid reservoir such that fluid flowing from the extrathoracic pump into the fluid treatment circuit returns directly to the fluid reservoir.

Figure 9:
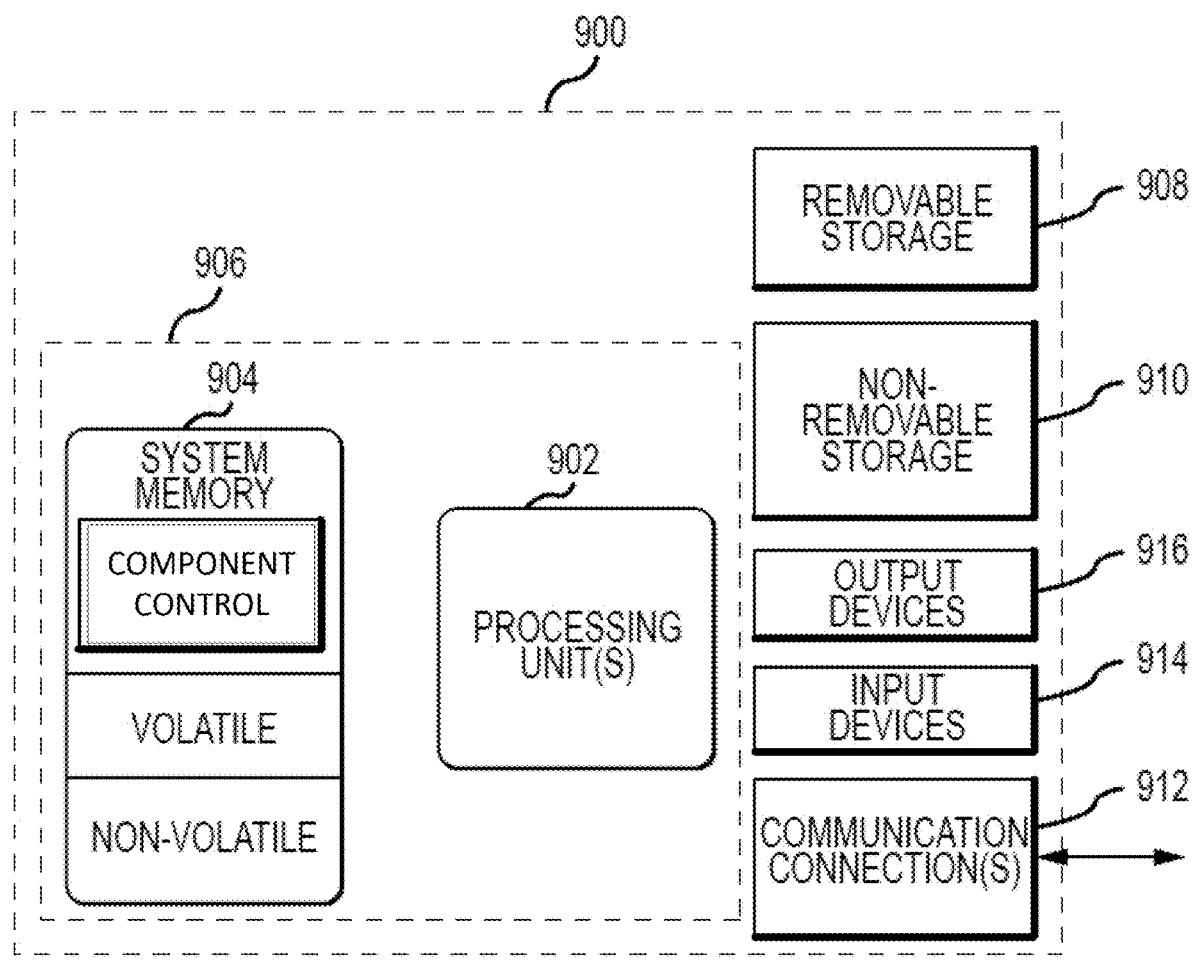
FIG. 9 depicts an example of a suitable operating environment in which one or more of the present examples can be implemented.

System 500 may further include controller 550. Controller 550 may be any suitable computer system having a processing engine and a memory module for, among other things, storing and executing instructions. FIG. 9, described in detail below, provides one example of a type of controller that may be used in system 500. Controller 550 may be communicatively coupled, such as by a wired or wireless connection, to one or more components of system 500. In nonlimiting examples, controller 550 is communicatively coupled with one or more of intrathoracic pump 506, pressurization vessel 532, extrathoracic pump 524, medicament introduction device 518, and any one or more of valves 504, 512, 514, 522, and 530. Additionally or alternatively, controller 550 may be communicatively coupled with one or more sensors placed within system 500 and/or associated with the components thereof. For instance, controller 550 may be communicatively coupled with pressure sensors 552, 554, flow sensors 556, blood flow sensors 558, pulse oximeter sensors, concentration sensors, temperature sensors, etc. These examples are nonlimiting and a person having skill in the art would appreciate a range of additional or alternative sensors that could be used advantageously in connection with system 500, in the various locations depicted in FIG. 1, or in other locations.

Controller 550 may be utilized to perform any of the methods disclosed herein, such as method 400 described below by controlling the operation of any one or more of the components of system 500, as well as variations thereon as would be apparent to a person of skill in the art upon reading this disclosure. Controller 550 may control the operation of valves 504, 512, 514, 522, and 530 so as to vary or adjust the intrathoracic pressure and extrathoracic pressure of a body B received by the receiver 538 or pressurization vessel 532. Control of valves 504, 512, 514, 522, and 530 may also avoid "choked" flow of fluid within system 500. While a person of skill in the art will appreciate that there are a number of alternative configurations of system 500, which offers a non-limiting example, Table 1 below summarizes component (e.g., the operation of valves, 504, 512, 514, 522, 530, and pumps 506 and 524) settings such that controller 550 may vary or adjust the flow of liquid in system 500. In Table 1, "ON" indicates a valve positioned to allow some amount of flow, full or partial, whereas "OFF" indicates a valve positioned not to allow flow.

TABLE 1

System Component Settings

| Operation | Valve 504 | Valve 512 | Valve 514 | Valve 522 | Valve 530 | Pump 506 | Pump 524 |
|---|---|---|---|---|---|---|---|
| Charge intrathoracic pump | ON | OFF | — | — | — | Extend | — |
| Increase intrathoracic pressure | OFF | ON | ON | — | — | Retract | — |
| Decrease intrathoracic pressure | — | OFF | ON | ON | OFF | — | Extend |
| Circulate fluid from body to circuit | — | — | — | OFF | ON | — | Retract |
| Increase extrathoracic pressure | — | — | — | OFF | ON | — | Retract |
| Decrease extrathoracic pressure | — | — | — | OFF | ON | — | Extend |
| Circulate fluid | — | — | OFF | ON | OFF | — | Retract |

TABLE 1-continued

System Component Settings

| Operation | Valve 504 | Valve 512 | Valve 514 | Valve 522 | Valve 530 | Pump 506 | Pump 524 |
|---|---|---|---|---|---|---|---|
| from extrathoracic pump to circuit | | | | | | | |

Beginning at the top of Table 1, intrathoracic pump 506 may be charged (e.g., filled with a fluid) by positioning valve 504 in an "ON" position, positioning valve 512 in an "OFF" position, and increasing the volume of pump chamber 510 by actuation of pump piston 508. Next, increased intrathoracic pressure may be applied by introducing liquid into a body B via controlled airway device 516. Intrathoracic pressure may be increased in this way by positioning valve 504 in an "OFF" position, positioning valve 512 in an "ON" position, positioning valve 514 in an "ON" position (e.g., a position to divert fluid flow into controlled airway device 516), and decreasing the volume of pump chamber 510 by actuation of pump piston 508. Conversely, intrathoracic pressure may be decreased by removing liquid from the body B via controlled airway device 516. Intrathoracic pressure may be decreased in this way by positioning valve 512 in an "OFF" position, positioning valve 514 in an "ON" position, positioning valve 522 in an "ON" position, positioning valve 530 in an "OFF" position and increasing the volume of pump chamber 528 by actuation of pump piston 526.

While fluid may be drawn out by applying a negative pressure to intrathoracic region of the body B, the fluid may alternatively be removed (or, more specifically, forced out) by application of a positive extrathoracic pressure. Accordingly, increasing the application of an extrathoracic pressure and circulating fluid from the body B into the liquid circuit may be accomplished by the same operation of valves and pumps. Specifically, both may be accomplished by positioning valve 522 in an "OFF" position, positioning valve 530 in an "ON" position, and decreasing the volume of pump chamber 528 by actuation of pump piston 526. When fluid flows into pressurization vessel 532, a force may be applied to the surface of the body B, thereby increasing extrathoracic pressure. At the same time, contraction of the intrathoracic region (e.g., due to compression of the chest cavity via the chest wall) may cause liquid within the intrathoracic region (e.g., within the lungs) to flow via controlled airway device 516 into the liquid circuit between valve 514 and valve 522.

Next, extrathoracic pressure may be decreased by removing liquid from the pressurization volume 536 of pressurization vessel 532. Extrathoracic pressure may be decreased in this way by positioning valve 522 in an "OFF" position, positioning valve 530 in an "ON" position, and increasing the volume of pump chamber 528 by actuation of pump piston 526. Finally, fluid may be circulated from pump chamber 528 to liquid treatment circuit 540. Such circulation may be accomplished by positioning valve 514 in an "OFF" position, positioning valve 522 in an "ON" position, positioning valve 530 in an "OFF" position and decreasing the volume of pump chamber 528 by actuation of pump piston 526

Optionally, controller 550 may additionally receive one or more signals from any of sensors 552, 554, 556, 558, or any other sensor placed within system 500 as required or desired. Controller 550 may control the operation of the components of system 500 based on the signal received from these or other sensors. For instance, controller 550 may receive a detected flow of blood within a body B received by pressurization volume 536. Based on the detected flow of blood, controller 550 may control the operation of intrathoracic pump 506 and/or extrathoracic pump 524, along with any one or more of the valves of system 500, to control the flow of fluid within system 500. For instance, controller 550 may, by controlling the flow of fluid within system 500, vary the application of an intrathoracic or extrathoracic pressure in order to induce a pressure gradient and increase or decrease the detected flow of blood within the body B. Controller 550 may monitor the volume and/or pressure of fluid within any element of system 500 by, for example, using a pressure sensor (e.g., pressure sensor 554) and/or a flow sensor (e.g., flow sensor 556). In this manner, controller 550 and system 500 may continuously or intermittently monitor the state of the fluid within system 500. Through such monitoring and/or controlling, system 500 may operate to induce a flow of blood in a circulatory system C of a body B received by the system 500.

Figure 6:
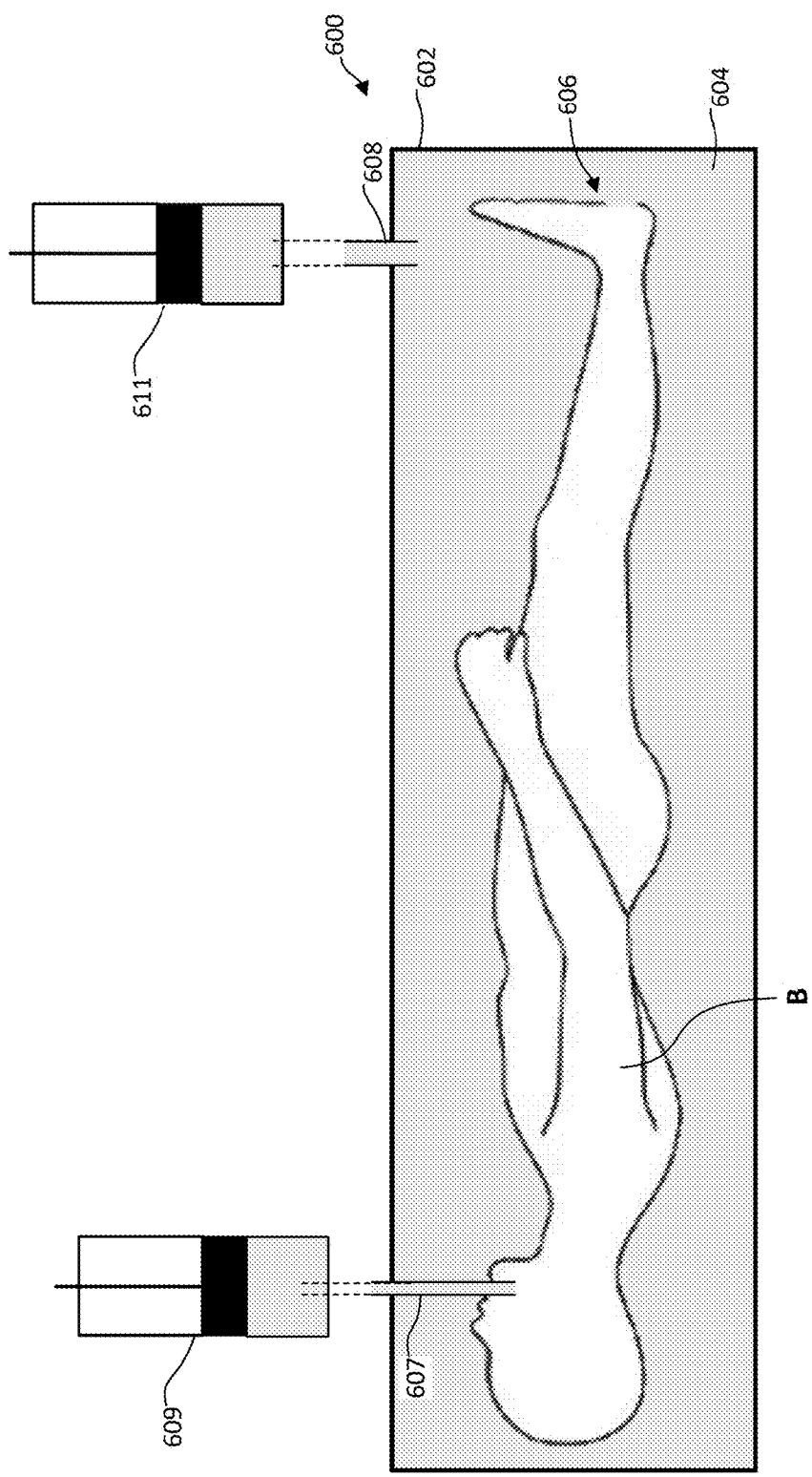
FIG. 6 is a schematic view of a pressurization vessel for a cardiovascular pumping system.

FIG. 6 depicts a schematic view of a pressurization vessel, 600, which may include a pressurization shell 602 and a pressurization volume 604, which may be a pressurizable bladder. Pressurization volume 604 may further define a receiver 606 into which a body B (e.g., human or other animal) may be received. In examples, receiver 606 is configured to receive a body B so as to allow introduction of a controlled airway device 607. A controlled airway device 607 may allow fluid connection between the body B and an intrathoracic pump 609. Pressurization volume 604 may further include port 608, which may be configured to allow the pressurization volume to be fluidly connected with an extrathoracic pump 611. An extrathoracic pump fluidly connected with port 608 of pressurization volume 604 may pump fluid from into pressurization volume 604. Such introduction of fluid into pressurization volume 604 may increase the pressure applied to a surface of the body B received by receiver 606 of pressurization volume 604.

Upon introduction of the fluid into pressurization volume 604, pressurization volume 604 may expand within pressurization vessel 600 (e.g., within the pressurization shell 602, which in examples is generally more rigid than the material that forms the pressurization volume 604). During such expansion, pressurization volume 604 exerts pressure at the surface of the body B in the receiver 606. Pressurization volume 604 may exert pressure at select locations or on select parts of the body B (e.g., at one or more extremities or limbs) of the body B or may exert pressure over substantially the entire surface of a body B. In some examples, pressurization volume 604 may receive a body B such that the body B is substantially enclosed within pressurization volume 604. In other examples, pressurization volume 604 may receive only a torso of the body B, e.g., in the form of a pressurization vest. In such examples, expansion of pressurization volume 604 exerts pressure to the surface of the torso of the body B. In these or other configurations, application of a pressure to one or more surfaces of the body B received in the pressurization volume 604 may be used to create a positive or negative pressure differential (e.g., "gradient") within the body B. For instance, the application of a pressure to a surface of the body B (e.g., by introduction of a fluid to the pressurization volume 604 by the extrathoracic pump 611) may increase a pressure in the vascular system of the body B (e.g., a mean systemic pressure). Such an increase may create a pressure differential between the systemic pressure and an intrathoracic pressure (e.g., a pressure of the right atrium). As is discussed in greater detail elsewhere herein, such a pressure gradient between an intrathoracic pressure and a pressure elsewhere in the body B and may induce a flow of blood from the body B into the heart (e.g., a venous return).

Figure 7:
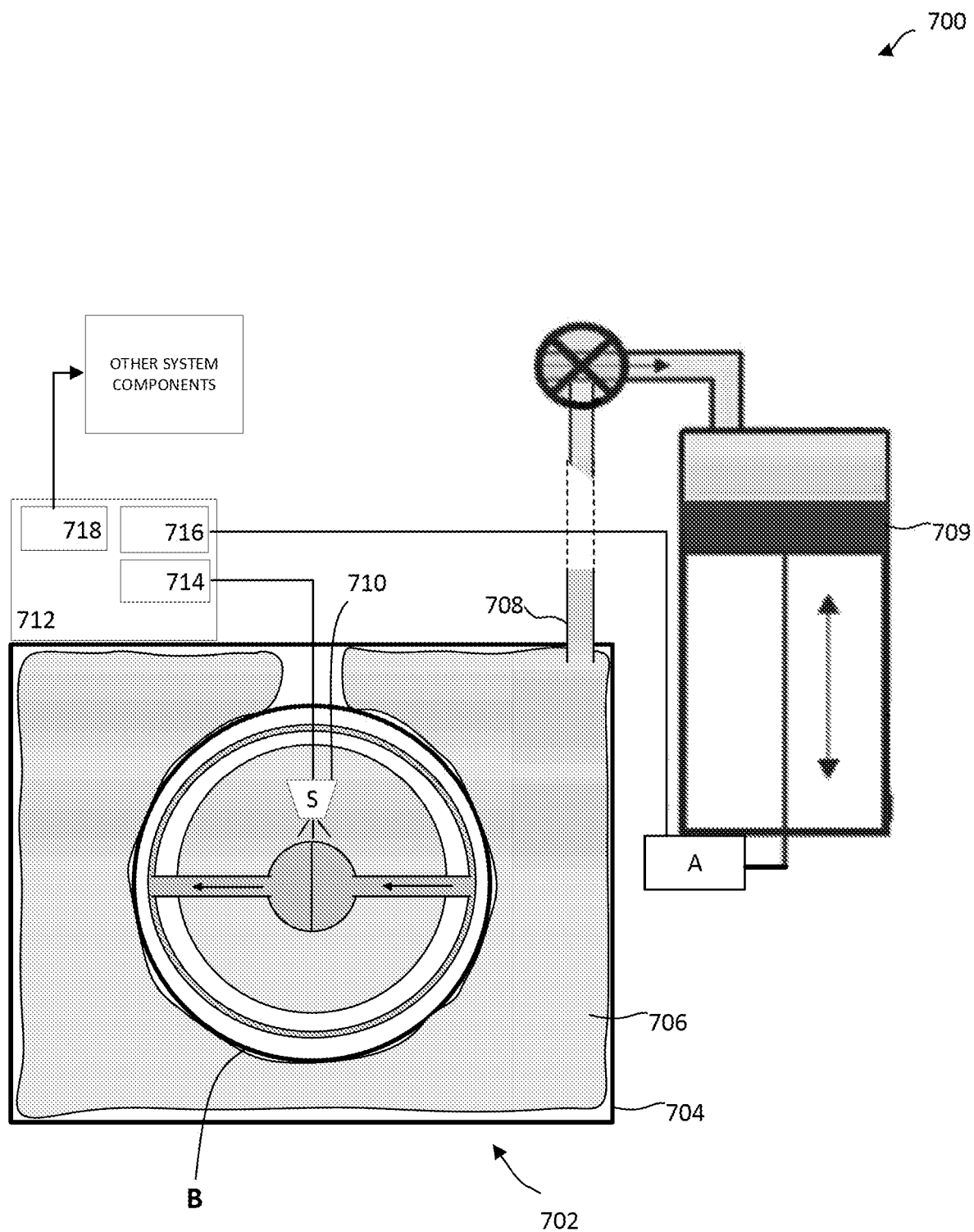
FIG. 7 is a schematic view of an example of a pressurization and control system for a cardiovascular pumping system.

FIG. 7 depicts a schematic view of an example of a pressurization and control system 700. The pressurization and control system may be a standalone, self-contained system with the required components, ports (both fluid and electrical), and other features to be utilized with the circuit and pumps depicted in FIG. 5. System 700 includes a pressurization vessel 702, which may include pressurization shell 704, pressurization volume 706, and port 708. Port 708 may be configured to be fluidly connected with one or more pumps of the system, such as extrathoracic pump 709, depicted for illustrative purposes. Port 708 receives fluid into pressurization volume 706 within pressurization shell 704, from extrathoracic pump 709. Receipt of liquid into pressurization volume 706 may induce expansion of pressurization volume 706, which may cause a force to be exerted at a surface of a body B received into pressurization vessel 702. Application or release of force at one or more points of contact with the surface of the body B may result in an extrathoracic pressure applied to the body.

System 700 may further include one or more sensors, such as sensor 710. As discussed elsewhere herein, application of an extrathoracic pressure may induce a flow of blood within a body B. Accordingly, sensor 710 may be a blood flow sensor capable of detecting an amount of flow of blood within a body. System 700 may, additionally or alternatively, include one or more pressure sensors, temperature sensors, fluid flow sensors, etc. Such sensors may be positioned in association with a component fluidly connected with system 700 (e.g., a flow sensor placed between pressurization volume 706 and the extrathoracic pump 709). Alternatively, such sensors may be configured to be positioned near or within a body and may be capable of detecting physiological data associated with the body (e.g., a perfusion sensor placed on an extremity of a body).

System 700 further includes controller 712. Controller 712 may be any suitable computer system having a processing engine and a memory module for, among other things, storing and executing instructions, such as the operating environment 900 depicted in FIG. 9. Controller 712, as shown, may be integrated with pressurization volume 702 and may include one or more control inputs and/or displays. Alternatively, controller 712 may be a partially integrated or standalone device. Controller 712 includes a plurality of auxiliary ports, 714, 716, and 718. Such auxiliary ports allow controller 712 to be communicatively coupled to one or more system components. For example, controller 712 is communicatively coupled (e.g., via a wired or wireless connection) with sensor 710 via auxiliary port 714, allowing information or conditions detected by sensor 710 to be transmitted to controller 712. As another example, controller 712 is communicatively coupled with extrathoracic pump 709 via auxiliary port 716. Controller 712 may include any number of auxiliary ports and such ports may enable connection to any number of system components (e.g., components of the system depicted as system 500). As shown, auxiliary port 718 is connected to other system components, such as any number of valves, pumps, sensors etc., allowing transmission of signals between controller 712 and any system component to which controller 712 is coupled. Auxiliary port 718 may include any number of auxiliary ports.

In an example, system 700 as depicted shows actuator A communicatively coupled with extrathoracic pump 709.

Actuator A can receive control signals from controller 712 related to the operation of any of the one or more components with which it is associated/coupled. For instance, controller 712 may transmit control signals relating to the operation of extrathoracic pump 709. Controller 712 may control operation of one or more components in response to signals received from sensor 710 or any other sensor associated with system 700. As an example, controller 712 may receive from sensor 10 an indication that a flow of blood in a body is lower than a desired threshold flow. In response, controller 712 may transmit a signal to actuator A associated with extrathoracic pump 709 to actuate the pump to fill pressurization volume 706 surrounding the body. In this example, introduction of liquid into pressurization volume 706 may increase an extrathoracic pressure applied to the body (e.g., at a surface of the body), thereby increasing the detected flow of blood to a desired threshold flow.

A person of skill in the art will understand that this is only one example of the signals that could be received by controller 712 from one or more sensors similar to sensor 710 and would understand that controller 712 may be communicatively coupled with any number and/or type of system components, such as multiple valves, pumps, and other devices through which controller 712 may control flow of a liquid through a system using any of the techniques described elsewhere herein.

Figure 8:
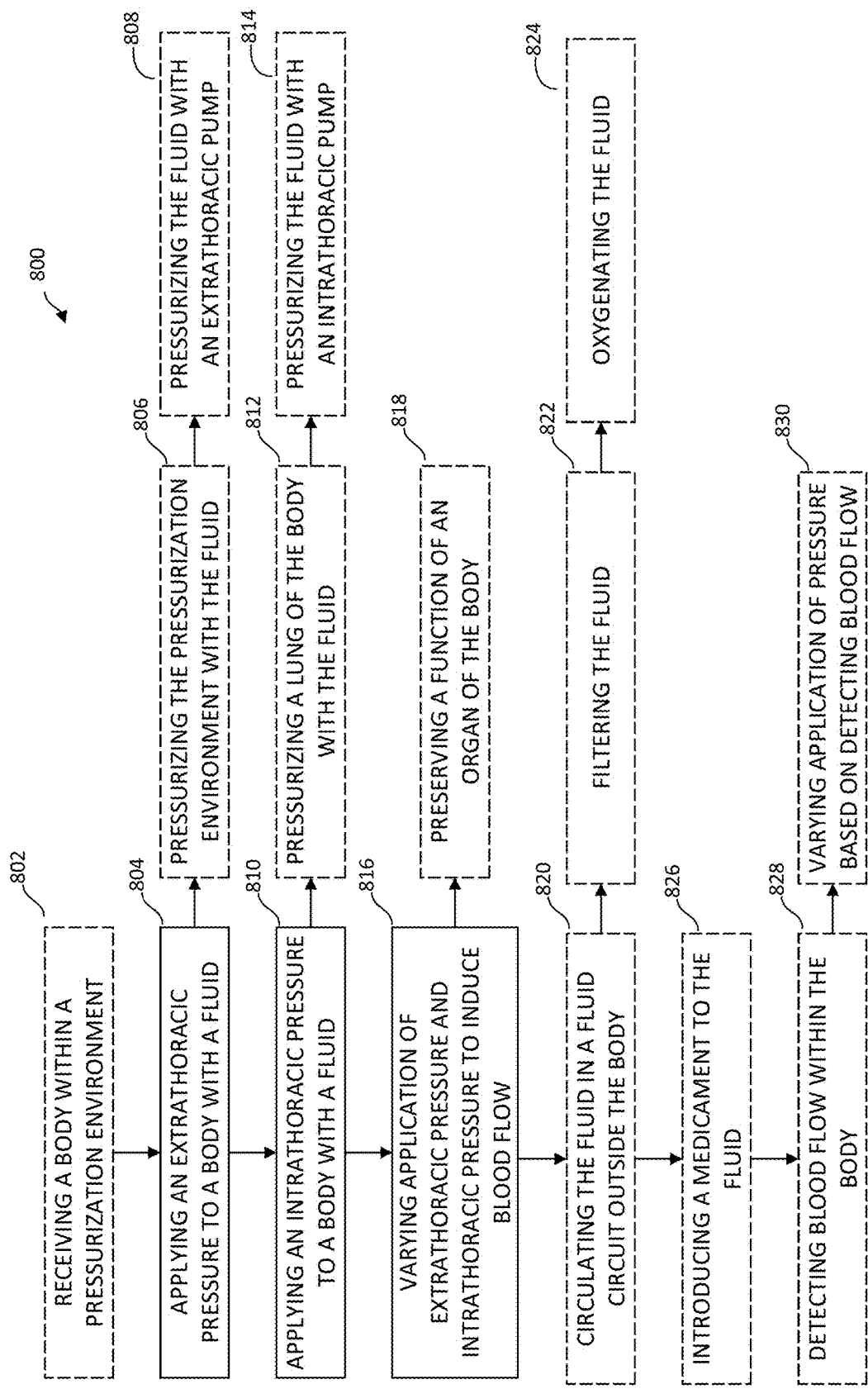
FIG. 8 depicts a method of circulating a flow of blood within a body.

FIG. 8 depicts a method 800 of inducing a flow of blood, such as a flow of blood within a cardiovascular system of a body. The method 800 may be implemented using a system for inducing blood flow, such as the systems described elsewhere herein. In brief, one such blood flow-inducing system includes a pressurization vessel that receives a body, an intrathoracic pump, and an extrathoracic pump. In an example, the method 800 may begin with optional operation 802, receiving the body within a pressurization environment. The method 800 includes applying an extrathoracic pressure to the body with a fluid, operation 804. Applying the extrathoracic pressure may include introducing a fluid into a pressurization environment, operation 806. Applying the extrathoracic pressure may include pressurizing the pressurization environment using an extrathoracic pump, operation 808. Pressurization environment may be a pressurization vessel, such as the pressurization vessels that are described elsewhere herein. Such pressurization vessels may include, in relevant part, a pressurization volume that may expand and contract (or inflate and deflate) around the body. In such an example, expansion of the pressurization volume results in application of force to an exterior (e.g., extrathoracic) portion (e.g., surface) of the body.

The method 800 continues with applying an intrathoracic pressure to the body with the fluid, operation 810. In an example, applying the intrathoracic pressure involves introducing a fluid into the lungs of the body, operation 812. Introducing the fluid into the lungs may be accomplished using an intrathoracic pump, operation 814, such as using a pump fluidly connected with the lungs of the body via a controlled airway device. In such an example, introduction of the fluid results in application of pressure to an interior (e.g., intrathoracic) portion (e.g., internal surface) of the body (e.g., within the chest cavity).

The method 800 continues by varying the application of the extrathoracic pressure and intrathoracic pressure, operation 816. As described elsewhere herein, differences in pressure (e.g., a "pressure gradient") between a heart's right atrium and the pressure of the circulatory system (e.g., the "mean systemic pressure") can induce vascular return (e.g., flow of blood from the vasculature to the heart). Conversely, a pressure gradient can induce cardiac output (e.g., flow of blood from the heart to the systemic circulatory system). In operation 816, varying application of extrathoracic pressure and intrathoracic pressure can result in such a pressure gradient in the body, including a pressure gradient sufficient to induce vascular return and/or cardiac output. Thus, at operation 816, method 800 may vary application of the extrathoracic pressure relative to the application of the intrathoracic pressure such that the application of pressure induces a flow of blood within the circulatory system of the body. As will be appreciated by one of skill in the art, the circulatory system may include a venous system and an arterial system, a systemic circulation, and a pulmonary circulation.

The varied application may include applying a positive extrathoracic pressure, or increasing the applied extrathoracic pressure, substantially simultaneously with applying a negative intrathoracic pressure for a predetermined time period. This application, or increase, may be followed by applying a negative extrathoracic pressure, or decreasing the applied extrathoracic pressure, substantially simultaneously with applying or increasing a positive intrathoracic pressure for a predetermined time period. This pressure application may be alternated at a predetermined frequency, as required or desired. In other examples, negative pressure need not be applied at all. Instead, positive extrathoracic pressure may be applied substantially simultaneously with no intrathoracic pressure, thus allowing excess pressure generated within the chest to be naturally relieved, which may prevent inadvertent damage to the lungs. In the next pressure cycle, a positive intrathoracic pressure may be applied substantially simultaneously with no extrathoracic pressure. To avoid inadvertent damage to the lungs, negative pressure may not be applied intrathoracically, while negative pressure may be applied to the pressurization volume to overcome losses associated with pressurizing that device. Positive, negative, or neutral pressure applications may be applied, regardless, as required or desired to meet particular blood flow requirements. In examples, the flow of blood may be sufficient to preserve certain function(s) of the organs of the body, operation 818. Such preservation may be the result of oxygen carried by the blood flow and delivered to the organs. In examples, the flow of blood achieved may be substantially similar to that of a human at rest or in systole.

Applying an extrathoracic pressure, operation 804, applying an intrathoracic pressure, operation 810, and varying the application of the extrathoracic and intrathoracic pressure, operation 816, may each include actuation or adjustment of one or more pumps or valves. For instance, by varying the configuration of valves and timing these configurations with the actuation of one or more pumps, method 800 may cause flow of a liquid between fluidly connected components in a way that causes application of positive or negative pressure to an extrathoracic or intrathoracic region of a body. An example of how a method 800 may vary the configuration of valves and actuation of pumps is provided in connection with system 100.

The method 800 continues with circulating the fluid in a fluid circuit disposed outside the body, optional operation 820. For instance, the fluid circuit may be a closed system fluidically connecting the extrathoracic pump, intrathoracic pump, and pressurization vessel. In such a configuration, circulating the fluid in the fluid circuit transfers the fluid from one component to the next (e.g., using the pressure applied by the extrathoracic pump and/or intrathoracic pump at operations 808, 814) during operation of method 800. Additionally or alternatively, circulating the fluid may include one or more of filtering the fluid and/or oxygenating the fluid, operations 822 and 824. The method 800 may further include introducing a medicament to the fluid, operation 826. In examples, introducing a medicament to the fluid, operation 826, may be included in circulating the fluid. As described elsewhere herein, filtering and oxygenating the fluid may enable and/or improve the delivery of oxygen to the lungs and, subsequently, to the blood. Similarly, introducing a medicament to the fluid may enable delivery of such a medicament to the body. The medicament could, for example, be any one or more of, independently or in combination, a pharmaceutical drug, a liquid mixture, a liquid compound, a solution, a solid compound, a vapor, etc. Thus, introducing the medicament at operation 826 may result in delivery of the medicament to the lungs, blood, organs, etc. during application of an intrathoracic pressure (e.g., at operations 810, 812, 814).

The method continues by detecting blood flow within the body, operation 828. In an example, an ultrasound sensor can be utilized to detect the blood flow within the body (e.g., using the Fick principle, thermal dilution, or dye dilution techniques). In another example, a monitoring sensor that measures transmitted, absorbed, and reflected light may be used. Sensors may be placed internal or external to the body. Additionally or alternatively, sensors may be placed in a cardiovascular pumping system, such as system 500. At operation 830, method 800 includes utilizing information determined by detecting the blood flow (e.g., at operation 828) to influence the varying of the application of the extrathoracic pressure and the intrathoracic pressure (e.g., in operation 816). In an example, method 800 detects blood flow at operation 828. If the blood flow detected at operation 828 is less than a determined desired amount of blood flow, the application of the extrathoracic pressure relative to the intrathoracic pressure may be modified. In an example, the amount of pressure applied may be increased or decreased. Alternatively, the timing of the application of the pressure may be modified. For instance, extrathoracic pressure applied at operation 804 may be applied either "in phase" with the application of intrathoracic pressure at operation 810, "out of phase" with operation 810, and/or some combination of the two. A person having ordinary skill in the art would understand the ways in which one might vary the application of extrathoracic pressure relative to the application of intrathoracic pressure based on detecting blood flow in a body.

FIG. 9 illustrates one example of a suitable operating environment 900 in which one or more of the present examples can be implemented. This operating environment may be incorporated directly into the systems disclosed herein, or may be incorporated into a computer system discrete from, but used to control the systems described herein. Such as computer system may be, e.g., a controller depicted elsewhere herein in conjunction with the pressure vessel, a controller disposed on and/or configured to transmit signals to one or more pumps or valves associated with the pressurization and control system depicted elsewhere herein, or a computer system used to monitor and control treatment of a patient, such as in a hospital setting. This is only one example of a suitable operating environment and is not intended to suggest any limitation as to the scope of use or functionality. Other well-known computing systems, environments, and/or configurations that can be suitable for use include, but are not limited to, imaging systems, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 900 typically includes at least one processing unit 902 and memory 904. Depending on the exact configuration and type of computing device, memory 904 (storing, among other things, instructions to control the pumps, valves, filters, heating element, oxygenators, reservoirs, sensors, or perform other methods disclosed herein) can be volatile (such as RAM), non-volatile (such as ROM, flash memory, etc.), or some combination of the two. This most basic configuration is illustrated in FIG. 11 by dashed line 906. Further, environment 900 can also include storage devices (removable, 908, and/or non-removable, 910) including, but not limited to, magnetic or optical disks or tape. Similarly, environment 900 can also have input device(s) 914 such as touch screens, keyboard, mouse, pen, voice input, etc., and/or output device(s) 916 such as a display, speakers, printer, etc. Also included in the environment can be one or more communication connections 912, such as LAN, WAN, point to point, Bluetooth, RF, etc.

Operating environment 900 typically includes at least some form of computer readable media. Computer readable media can be any available media that can be accessed by processing unit 902 or other devices having the operating environment. By way of example, and not limitation, computer readable media can include computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media. A computer-readable device is a hardware device incorporating computer storage media.

The operating environment 900 can be a single computer operating in a networked environment using logical connections to one or more remote computers. The remote computer can be a personal computer, a server, a router, a network PC, a peer device or other common network node, and typically includes many or all of the components described above as well as others not so mentioned. The logical connections can include any method supported by available communications media. Such networking environments are commonplace in offices, enterprise-wide computer networks, intranets and the Internet.

In some embodiments, the components described herein include such modules or instructions executable by computer system 900 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 900 is part of a network that stores data in remote storage media for use by the computer system 900.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. A method of circulating a flow of blood within a circulatory system of a body with a surface area, the method comprising:
   applying a positive extrathoracic pressure across substantially all of the surface area of the body with a fluid within a pressurization vessel;
   applying a positive intrathoracic pressure to the body with the fluid;
   applying a negative extrathoracic pressure across substantially all of the surface area of the body with the fluid by depressurizing the pressurization vessel;
   applying a negative intrathoracic pressure to the body with the fluid; and
   varying the application of the positive extrathoracic pressure relative to the application of the positive intrathoracic pressure and the application of the negative extrathoracic pressure relative to the application of the negative intrathoracic pressure, so as to circulate the blood flow within the circulatory system of the body.

2. The method of claim 1, further comprising receiving the body within the pressurization vessel.

3. The method of claim 2, wherein applying the extrathoracic pressure comprises pressurizing the pressurization environment with the fluid, wherein the fluid is pressurized and depressurized by an extrathoracic pump.

4. The method of claim 1, wherein applying the intrathoracic pressure comprises pressurizing a lung of the body with the fluid, wherein the fluid is pressurized and depressurized by an intrathoracic pump.

5. The method of claim 1, further comprising circulating the fluid in a fluid circuit disposed outside of the body.

6. The method of claim 5, wherein circulating the fluid further comprises filtering the fluid.

7. The method of claim 6, wherein circulating the fluid further comprises oxygenating the fluid.

8. The method of claim 1, further comprising introducing at least one medicament to the fluid.

9. The method of claim 1, wherein the circulation of the blood flow within the circulatory system of the body is sufficient to preserve a function of at least one organ of the body.

10. The method of claim 1, further comprising detecting the circulation of the blood flow within the circulatory system of the body, wherein varying the application of the positive extrathoracic pressure relative to the application of the positive intrathoracic pressure and the application of the negative extrathoracic pressure relative to the application of the negative intrathoracic pressure is based at least in part on detecting the circulation of the blood flow within the circulatory system of the body.

11. A system for circulating a blood flow within a circulatory system of a body with a surface area, the system comprising:
   a pressurization vessel configured to receive the body and a fluid;
   an extrathoracic pump fluidically coupled to the pressurization vessel and configured to:
      apply a positive extrathoracic pressure across substantially all of the surface area of the body by pressurizing the pressurization vessel; and
      apply a negative extrathoracic pressure across substantially all of the surface area of the body with the fluid by depressurizing the pressurization vessel;
   an intrathoracic pump configured to be fluidically coupled to a controlled airway device inserted into the body and configured to:
      apply a positive intrathoracic pressure to the body with the fluid; and
      apply a negative intrathoracic pressure to the body with the fluid; and
   a fluid treatment circuit fluidically coupled to the extrathoracic pump and the intrathoracic pump.

12. The system of claim 11, wherein the fluid treatment circuit comprises at least one of a fluid heater, a fluid cooler, a fluid filter, a fluid oxygenator, a fluid carbon dioxide scavenger, a fluid reservoir, and a fluid medicament introduction structure.

13. The system of claim 11, wherein at least one of the extrathoracic pump and the intrathoracic pump comprises a dynamic pump.

14. The system of claim 11, wherein the pressurization vessel comprises:
   an exterior shell; and
   an interior bladder disposed within the exterior shell.

15. The system of claim 14, wherein the exterior shell is integral with the interior bladder.

16. The system of claim 14, wherein the exterior shell is rigid and the interior bladder is flexible.

17. The system of claim 11, further comprising:
   a controller communicatively coupled to the extrathoracic pump and the intrathoracic pump; and
   a sensor for sensing the blood flow within the circulatory system of the body.

18. The system of claim 17, wherein the sensor comprises an ultrasound sensor.

19. The system of claim 11, wherein the pressurization vessel comprises a pressurizable sleeve.

20. A system comprising:
   a pressurization vessel comprising a port configured to connect the pressurization vessel to a fluid pump, wherein the pressurization vessel at least partially defines a receiver for receiving a body with an extrathoracic surface area and an intrathoracic lung volume;
a sensor for detecting a condition within the body when the body is received within the receiver, and
a controller configured to be communicatively coupled to the sensor, wherein the controller comprises at least one auxiliary input for connecting the controller to the fluid pump and wherein the controller is configured to control the fluid pump to:
  pressurize the pressurization vessel to apply a positive extrathoracic pressure across substantially all of the extrathoracic surface area of the body;
  depressurize the pressurization vessel to apply a negative extrathoracic pressure across substantially all of the extrathoracic surface area of the body;
  apply a positive intrathoracic pressure to the intrathoracic lung volume with the fluid;
  apply a negative intrathoracic pressure to the intrathoracic lung volume with the fluid; and
  vary, based on communications with the sensor, the application of the positive extrathoracic pressure relative to the application of the positive intrathoracic pressure and the application of the negative extrathoracic pressure relative to the application of the negative intrathoracic pressure, so as to circulate the blood flow within a circulatory system of the body.

* * * * *